United States Patent [19]

Maeda et al.

[11] Patent Number: 4,762,885
[45] Date of Patent: Aug. 9, 1988

[54] NEOCARZINOSTATIN DERIVATIVES AND A PROCESS FOR MANUFACTURING THE SAME

[75] Inventors: Hiroshi Maeda, 631-3, Aza-Tamukae, Hotakubohon-Machi, Kumamoto City, Kumamoto Pref.; Ryunosuke Kanamaru; Nakao Ishida, both of Sendai; Toshihiko Yoshitake, Kurashiki; Minoru Ueda, Okayama, all of Japan

[73] Assignees: Kuraray Co., Ltd., Kurashiki; Yamanouchi Pharmaceutical Co., Ltd.; Kayaku Antibiotics Research Co., Ltd., both of Tokyo; Hiroshi Maeda, Kumamoto, all of Japan

[21] Appl. No.: 911,456

[22] Filed: Sep. 25, 1986

Related U.S. Application Data

[63] Continuation of Ser. No. 749,679, Jun. 28, 1985, abandoned, which is a continuation of Ser. No. 636,485, Aug. 1, 1984, abandoned.

[30] Foreign Application Priority Data

Aug. 8, 1983 [JP]  Japan ................................ 58-145419

[51] Int. Cl.⁴ ...................... A61K 31/785; C08F 8/32
[52] U.S. Cl. ..................................... 525/54.1; 424/78
[58] Field of Search ................ 525/54.1, 54.11, 328.2; 526/272, 238.1; 424/78; 260/DIG. 47

[56]  References Cited

U.S. PATENT DOCUMENTS 3,085,994  4/1963  Muskat ................................. 526/272
3,121,043  2/1964  Tobin et al. ....................... 525/327.6
3,245,933  4/1966  Muskat ................................. 526/272
4,182,752  1/1980  Maeda et al. ............... 260/DIG. 47

Primary Examiner—Delbert R. Phillips
Assistant Examiner—Nathan M. Nutter
Attorney, Agent, or Firm—Burns, Doane, Swecker & Mathis

[57]  ABSTRACT

Substantially pure neocarzinostatin anticancer agents have the formula (A):

(SMA)-(NCS)-(SMA)   (A)

wherein (NCS) is a divalent neocarzinostatin residue and (SMA) comprises the monovalent residue of a styrene-maleic acid copolymer having a weight-average molecular weight of from 800 to 2,500, said (NCS) residue being bonded to said (SMA) residues via amide linkages formed between primary amino groups of the neocarzinostatin molecule and carbonyl groups of the styrene-maleic acid copolymer.

19 Claims, 5 Drawing Sheets

FIG. 1

Chemical Shift (ppm)

FIG_4a

FIG_4b

FIG_6

NEOCARZINOSTATIN DERIVATIVES AND A PROCESS FOR MANUFACTURING THE SAME

This application is a continuation of application Ser. No. 749,679, filed June 28, 1985, now abandoned, which is a continuation of now abandoned U.S. Ser. No. 636,485 of Aug. 1, 1984.

BACKGROUND OF THE INVENTION

1. Field of the Invention

The present invention relates to neocarzinostatin derivatives having excellent anticancer activity, which have the following formula $$(SMA)\text{-}(NCS)\text{-}(SMA) \qquad (I)$$

wherein (NCS) represents divalent neocarzinostatin residue in which one hydrogen atom is removed from each of the primary amino group in alanine residue at the N-terminal of neocarzinostatin and that in lysine residue at 20th position from the N-terminal of neocarzinostatin and (SMA) represents monovalent styrene-maleic acid copolymeric residue having a weight-average molecular weight of 800~2,500 and consisting of structural units of styrene residue maleic acid residue and a residue having the following formula in which a hydroxyl group of one carboxyl group in the maleic acid residue is removed and linked to neocarzinostatin residue wherein the linkage of carbon atom in carbonyl group bonds to the neocarzinostatin residue, and a process for manufacturing the same.

2. Description of the Prior Arts

Neocarzinostatin (abbreviated as "NCS" hereinafter) is a proteinaceous anticancer agent produced in a medium in which Streptomyces carzinostaticus var. F-41 Kuroya is cultured (Japanese Patent Publication No. 42 (1967)-21,752 and U.S. Pat. No. 3,334,022). With respect to the primary structure of this substance, the total number of amino acid residues and estimated molecular weight have been reported to be 109 and 10,700 respectively, by Hiroshi Maeda who is one of the present inventors (Science, 178, 875–876 (1972) and Arch. Biochem. Biophys., 163, 379–385).

In the treatment of cancer, the metastasis of cancer cells is important and particularly the metastasis of said cells into lymphatic system is the most important problem. A wide variety of neocarzinostatin derivatives have been examined with the aim of lowering the toxicity, prolonging the biological activity of the drug in vivo, and directing its delivery more to the lymphatic system. As a result, it has been found that neocarzinostatin derivatives having the following formula (II), which is obtained by reacting two primary amino groups present in the molecule of neocarzinostatin with a partially hydrolyzed styrene-maleic anhydride copolymer having a molecular weight of 2,500~80,000 (the partially hydrolyzed styrene-maleic anhydride copolymer is abbreviated as "H-SMA" hereinafter), possess the above described activities and this has been disclosed in U.S. Pat. No. 4,182,752.

$$(SMA')\text{-}(NCS)\text{-}(SMA') \qquad (II)$$

wherein (NCS) means the same NCS residue as in the above described formula (I) and (SMA') means styrene maleic acid copolymeric residue having an average molecular weight of 2,500~80,000.

However, the above described NCS derivatives may contain various molecular species even after purification by the gel filtration method and the like. Concerning this point, the inventors have studied more rigorously and found that when NCS is reacted with H-SMA in an aqueous medium, the reaction solution after the completion of the reaction includes, other than the aimed NCS derivative, styrene-maleic acid copolymer produced by ring-opening hydrolysis of the maleic anhydride ring in H-SMA (referred to as "ring-opening hydrolyzed" product of H-SMA" hereinafter), unreacted NCS, an intermediate product to NCS derivative (I) having the following formula (III)

$$(NCS')\text{-}(SMA'') \qquad (III)$$

wherein (NCS') represents monovalent NCS residue in which one hydrogen atom is removed from each of the primary amino group in alanine residue at the N-terminal of neocarzinostatin and that in lysine residue at 20th position from the N-terminal of neocarzinostatin, and (SMA'') represents monovalent styrene-maleic acid copolymeric residue consisting of styrene residue, maleic acid residue and a residue having a formula in which hydroxyl group in carboxyl group has been replaced by nitrogen of the said amino group in NCS residue, and by-products having the following formulae (IV), (V) and (VI)

$$(SMA'')\text{+}(NCS)\text{—}(SMA''')\overline{)_m}\text{—}(NCS)\text{—}(SMA) \qquad (IV)$$

$$(SMA'')\text{+}NCS)\text{—}(SMA''')\overline{)_m}\text{—}(NCS') \qquad (V)$$

$$(NCS')\text{+}(SNA''')\text{—}(NCS)\overline{)_{m-1}}\text{—}(SMA''')\text{—}(NCS') \qquad (VI)$$

wherein (NCS) has the same meaning as in the formula (I), (NCS') has the same meaning as in the formula (III), (SMA'') has the same meaning as in the formula (III), and (SMA''') represents bivalent styrene-maleic acid copolymeric residue comprising styrene residue, maleic acid residue and two residues, each having a formula in which hydroxyl group is removed from one carboxyl group in maleic acid residue and bonded to NCS residue and m represents 1 or 2, and these impurities cannot be satisfactorily removed in the separation and purification step, such as gel filtration and the like and are admixed in the aimed NCS derivatives.

SUMMARY OF THE INVENTION

The inventors have intensively studied so as to manufacture substantially pure NCS derivatives and found that by reacting NCS with H-SMA in an excessive amount of H-SMA resulted in a high rate of reaction, the unreacted NCS and the intermediate product (III) are essentially undetectable and by using H-SMA having an adequately smaller molecular weight and a narrow molecular weight distribution, the difference of molecular size between the aimed NCS derivative and the ring-opening hydrolyzed product of H-SMA can be enlarged so that the isolation of the aimed NCS derivatives can be easily achieved by gel filtration, and the present invention has been accomplished.

That is, the present invention lies in NCS derivatives shown by the above described formula (I) and a process for manufacturing NCS derivatives, which comprises reacting H-SMA satisfying the following formulae (VII) and (VIII)

$$800 \leq \overline{M}w < 2{,}500 \quad \text{(VII)}$$

$$\overline{M}w/\overline{M}n \leq 1.5 \sim 1.1 \times 10^{-4} \overline{M}w \quad \text{(VIII)}$$

wherein $\overline{M}w$ means a weight-average molecular weight of H-SMA and equation (VII) is allowed to have any $\overline{M}w$ from 800 to 2,500, and $\overline{M}n$ means a number-average molecular weight of H-SMA, with NCS in an aqueous medium by adding a large excess of powdery H-SMA based on the molar ratio of H-SMA to NCS, and then subjecting the reaction product to gel filtration to isolate the NCS derivative which conforms to the above described formula (I).

When the biological activity based on the growth inhibition of Sarcina lutea (abbreviated as "biological assay" hereinafter) which has been known to be parallel to the antitumor activity (reported by N. Ishida, K. Miyazaki, K. Kumagai and M. Rikimaru, J. Antibiot (Tokyo), Serial A18, 68 (1965) is examined with respect to NCS derivatives of the present invention, it has been found that the activity of these NCS derivatives (I) surprisingly have a high activity comparable to NCS. This is presumably because NCS derivatives of the present invention are different from the prior NCS derivatives shown by the formula (II) and do not substantially contain impurities, and since the molecular weight of styrene-maleic acid copolymeric residue is small, the biological activity based on NCS residue is not substantially diluted. Furthermore, in such NCS derivatives, the toxicity possessed by NCS is moderated and the specific accumulation to the lymphatic system and the retention of the activity in blood, which are deficient in NCS are improved, so that such NCS derivatives serve as a very excellent anticancer activity.

DESCRIPTION OF THE PREFERRED EMBODIMENTS

Detailed explanation will be made with respect to the NCS derivatives (I) of the present invention.

Firstly, explanation is made with respect to the structure of the NCS derivatives (I). The NCS derivatives (I) are formed by bonding one NCS residue with two styrene-maleic acid copolymeric residues through acid amide linkages. The NCS residue is a protein having two primary amino groups, one at N-terminal alanine (at position 1) and lysine group at the position 20th from the N-terminal as disclosed in the above described literature [Science, 178, 875~876 (1972)]. An NCS molecule contains a large number of functional groups, such as hydroxyl groups and secondary amino groups other than two primary amino groups but in the NCS derivatives of the present invention, the functional groups other than two primary amino groups do not substantially serve to form chemical bonds with the styrene-maleic acid copolymeric residue. Namely, the NCS residue which is one of the structural components of the NCS derivative (I) of the present invention, serves to form a bivalent residue in NCS derivative (I) in which one hydrogen atom is removed from each of the above described two primary amino groups in NCS, that is, in total, two hydrogen atoms are removed.

The styrene-maleic acid copolymeric residue, which is another structural component in NCS derivative of the present invention, consists of the structural units of (a) styrene residue (b) maleic acid residue, and (c) a residue having the following formula in which a hydroxyl group from one carboxyl group in the maleic acid residue is removed and linked to the neocarzinostatin residue wherein the linkage of carbon atom of carbonyl group bonds to NCS residue, and has a weight-average molecular weight of 800~2,500.

Such a weight-average molecular weight can be determined by the manner disclosed in the examples mentioned hereinafter. The smaller the weight-average molecular weight of these copolymeric residues, the more easy the separation of NCS derivative from the reaction product is but NCS derivatives having the copolymeric residue wherein the weight-average molecular weight is less than 800 are difficultly used in practice. In the above described copolymeric residue, the residue (c) is formed by reacting maleic anhydride residue in H-SMA of the starting material with the primary amino group in NCS and opening the anhydride ring. One part of the residue (b) corresponds to maleic acid residue in H-SMA as such and another part is ones formed through hydrolysis of maleic anhydride residue in H-SMA not reacted with NCS in an aqueous medium. The residue (a) corresponds to styrene residue in H-SMA as such. Thus, the ratio of these residues (a), (b) and (c) in the styrene-maleic acid copolymeric residue varies depending upon selection of the polymer composition of H-SMA, so that the composition ratio of each residue in the styrene-maleic acid copolymeric residue lies in the practical range for industrial purpose.

In the production of the NCS derivatives of the present invention, the selection of the H-SMA subjected to the reaction with NCS is important and explanation will be made with respect to this point. As mentioned above, H-SMA consists of styrene residue (a'), maleic acid residue (b') and maleic anhydride residue (c'). The molar ratio of the residue (A') to the sum of the residue (b') and the residue (c') in H-SMA is preferred to be substantially about 1:1~1.3:1, more preferably about 1:1. Such ratio is mainly selected in view of the solubility of the H-SMA in an aqueous medium when H-SMA is reacted with NCS while being dissolved in the aqueous medium. The higher the ratio of the hydrophobic residue (a') in H-SMA, the lower the solubility of H-SMA in the aqueous medium. It is practically impossible to obtain H-SMA having the ratio of the residue (a') being smaller than 1 in the copolymerization of styrene with maleic anhydride.

Concerning the ratio of the residue (b') to the residue (c'), by taking both the solubility of H-SMA in an aqueous medium and the reactivity of H-SMA with NCS into consideration, the molar ratio of the residue (b') to the residue (c') is preferred to be 85:15~35:65, more preferably 80:20~40:60. If the content of the residue (c') in H-SMA is less than 15 mol%, the rate of reaction of the amino groups of NCS with the H-SMA is so low that the presence of considerable amount of unreacted NCS is unavoidable. On the other hand, if the content of the residue (c') exceeds 65 mol%, the rate of dissolution of the E-SMA in the reaction medium is so low that the reaction does not take place spontaneously.

The H-SMA having the above mentioned constitution is preferable as the starting material of the present invention but the average molecular weight and the molecular weight distribution of H-SMA must be within the ranges shown by the above described formulae (VII) and (VIII). The formula (VII) corresponds to the average molecular weight of the styrene-maleic acid copolymeric residue in the already defined NCS derivatives. The H-SMA subjected to the modification reaction of the NCS has a narrow distribution and thus the species of H-SMA having higher molecular weights in such a distribution may be adequately high in the reactivity with NCS because the average content of maleic anhydride residue, at which the reaction takes place with NCS, is higher and the probability is high and the probability to form the styrene-maleic acid copolymeric residue in NCS derivative after reaction with NCS is also higher. Consequently, in a strict sense, the weight-average molecular weight of the H-SMA and the average molecular weight of the copolymeric residue in the NCS derivates thus formed are different in exactness and the value of the latter tends to be more or less higher than that of the former. However, as seen from the examples mentioned hereinafter, this difference is not so high and it is permissible to consider that the weight-average molecular weight of H-SMA is practically equal to the average molecular weight of the styrene-maleic acid copolymeric residue.

For the production of the NCS derivatives (I) of the present invention, it is important to use H-SMA having the weight average molecular weight as shown by the formula (VII) and the specifically narrow molecular weight distribution ($\overline{M}w/\overline{M}n$) shown by the formula (VIII). When the reaction product of NCS with H-SMA is subjected to gel filtration, the aimed NCS derivatives of the present invention elute faster than the hydrolyzed and ring-opened product of H-SMA but both of these substances tend to elute simultaneously to a considerable extent and this is a great problem in the isolation of NCS derivatives. However, when H-SMA, in which the average molecular weight and the molecular weight distribution have been adjusted as described above, is used for the reaction with NCS, the difference between the molecular size of the NCS derivatives (I) formed and the ring-opening hydrolyzed product of H-SMA in solution is sufficient to isolate substantially pure NCS derivative (I). Consequently, the separability of NCS derivative (I) and the ring-opening hydrolyzed product of H-SMA is improved and the isolation of NCS derivative (I) becomes feasible. None of the separation methods except gel filtration was able to achieve satisfactory isolation of the present NCS derivative.

In the manufacture of the NCS derivatives of the present invention, the above mentioned H-SMA is used but the constitution of the styrene-maleic acid copolymeric residue of the NCS derivative formed depends on the H-SMA used. Such H-SMA is obtained by partially hydrolyzing styrene-maleic anhydride copolymer (abbreviated as "SMA" hereinafter). However, SMA produced by the usual polymrization has broad molecular weight distribution and the molecular weight distribution index ($\overline{M}w/\overline{M}n$) is about 2.0 or more.

The H-SMA obtained by partially hydrolyzing such SMA also maintains such a broad molecular weight distribution, so that even if NCS is reacted with H-SMA sufficiently, it is difficult to isolate the aimed NCS derivative (I) from the reaction mixture. Therefore, it is necessary to refine the molecular weight distribution by effecting fractionation of the SMA having a broad molecular weight distribution before or after partial hydrolysis, in which SMA has been obtained through usual polymerization process (for example, styrene and maleic anhydride are subjected to a solution polymerization at a temperature of 90°~200° C. in a solvent (cumene, p-cymene, ethylbenzene, etc.) having a function as a chain transfer agent by using benzoyl peroxide, dicumyl peroxide, etc. as an initiator according to Japanese Patent Publication No. 47(1972)-44,552 and U.S. Pat. No. 3,245,933). As the fractionating process, use may be made of solubility process or ultrafiltration process and the like, but the most preferable one comprises fractionating SMA through fractional solution process and partially hydrolyzing the obtained SMA having a narrow molecular weight distribution to convert SMA into H-SMA having the narrow molecular weight distribution.

Thus obtained H-SMA is reacted with NCS in an aqueous medium. As seen from the structural formula (I) of NCS derivatives, it is merely necessary to react two molecules of H-SMA per one molecular of NCS, so that the ideal amount of H-SMA required is 2 moles based on 1 mole of NCS. But, in reality, as mentioned above, maleic anhydride residue portion in H-SMA reacts competitively with the primary amino group, hydroxyl group in NCS molecule and water molecule and some other functional residues in NCS molecule. Some of the reaction products thus formed are hydrolyzed to yield maleic acid residue. Some of the anhydride residue in H-SMA are hydrolyzed in the reaction condition and its ring is opened and converted into styrene-maleic acid copolymer. When the ring of the anhydride is opened, the products can no longer react with NCS. Thus, H-SMA must be used in large excess of the theoretical molar ratio with respect to NCS. Since the weight-average molecular weight of H-SMA is 800~2,500 as shown by the formula (IV) and the molecular weight of NCS is 10,700, even though the amount of H-SMA used varies depending upon the average molecular weight, said amount must be more than 0.15 part by weight in the case of H-SMA having a weight average molecular weight of 800 and 0.47 part by weight in the case of H-SMA having a weight-average molecular weight of 2,500. In particular, when the average molecular weight of H-SMA is small or the content of maleic anhydride residue is low, the average number of maleic anhydride residue contained per one molecule is small and such H-SMA is high in the raio of H-SMA molecule having no maleic anhydride residue (having no reactivity with NCS), so that it is important to use a high molar excess of H-SMA. In order to increase the extent of reaction of primary amino groups in NCS with H-SMA to a sufficiently high level, it is preferred to use 1.5–15 parts by weight and more preferably 2–12 parts by weight of H-SMA based on 1 part by weight of NCS, although the amount of H-SMA required to achieve the above condition depends upon the average molecular weight and structure of the H-SMA as described above. When the amount of H-SMA used is more than 15 parts by weight based on 1 part by weight of NCS, the reaction product in a reaction mixture is diluted so much by the ring-opening hydrolyzed product of H-SMA that in the subsequent separation will be poor and thus such an amount of H-SMA is not feasible and the use of such a large amount is impractical.

In the reaction of NCS with H-SMA, the total concentration of NCS and H-SMA in the reaction solution is preferred to be 10~35% by weight and more preferably 15~32% by weight. When the total concentration in the reaction solution is lower than 10% by weight, the rate of reaction of NCS with H-SMA is low and the chance where maleic anhydride residue in H-SMA is hydrolyzed is increased, causing a difficulty in obtaining desired derivative of NCS. Conversely, when the total concentration of NCS and H-SMA exceeds 35% by weight, the viscosity of the reaction solution is so high that the stirring of the reaction mixture becomes difficult and such a condition is not desirable.

The reaction of NCS with H-SMA is generally effected by firstly dissolving NCS is an aqueous solution of sodium bicarbonate, sodium acetate, ammonium bicarbonate and the like and then adding stepwise powdery H-SMA to this solution. The concentration of these aqueous salts is not specifically defined but it is preferably to maintain the pH of the aqueous solution at 7.5–9.5, preferably 8.0–8.7. When pH of the solution is lower than 7.5, H-SMA is insoluble or difficultly soluble in the aqueous medium. In the former case, it is impossible to proceed the reaction with the primary group of NCS to any extent, while in the latter, a very long time is needed for the dissolution and such a pH is not practicable. When pH of the reaction solution is higher than 9.5, it is possible that the biological activity of the NCS derivatives in the solution decreases and such pH also is thus undesirable. Furthermore, in order to maintain the biological activity of the NCS derivatives, it is preferable to react at a temperature lower than 15° C. in the dark.

By selecting the above described reaction conditions appropriately, the conversion of the primary amino group in NCS in the reaction of NCS with H-SMA can exceed as high more than 95 mol% and 100 mol% may be easily obtained. When such a high conversion is attained, unreacted NCS is practically undetectable and an amount of the intermediate by-product shown by the formula (III) which is formed by reacting only one of the two primary amino groups of NCS with H-SMA is very low. On the other hand, although the increase of the by-products shown by the formulae (IV), (V) and (VI) is expected to increase in parallel with the increase in the degree of the conversion of the primary amino group of NCS, it has been found that the amount of these by-products are unexpectedly low and the yield of the object product of the present invention is very high. These by-products can be separated and removed during the purification process mentioned hereinafter.

Then, the NCS derivatives of the present invention are isolated from the reaction mixture by the gel filtration method. The substrate to be used in the gel filtration is selected from ones having an exclusion limit as expressed in the molecular weight of 50,000~150,000, preferably 60,000~100,000 for globular protein and the most preferable substrate to obtain the NCS derivatives (I) of the present invention can be selected from the following commercially available gel particles; Sephadex G-50, G-75, G-100 (made by Pharmacia Fine chemicals AB, Uppsala, Sweden) and Bio-Gel P-60, P-100 (made by Bio-Rad Laboratories, U.S.A.). Other desirable gel filtration conditions may be arbitrarily selected. In order to efficiently carry out the gel filtration efficiently, it is preferable to perform the preliminary purification of the reaction solution after completion of reaction of NCS with H-SMA by dialysis or ultrafiltration by means of a dialysis tube or an ultrafiltration membrane in which the cut-off molecular weight of the globular protein is about 10,000, to remove the salt and concurrently partially remove the ring-opening hydrolyzed product of H-SMA which remained unreacted with NCS. Alternatively, the NCS derivatives of the present invention may be isolated by subjecting the reaction solution to a preliminarily purification through a gel filtration and then to an additional gel filtration.

The NCS derivatives (I) of the present invention are separated from the other reaction products during the above described gel filtration. Then, the eluate cut containing the NCS derivtives (I) is subjected to lyophilization to remove the solvent, whereby NCS derivatives (I) of the present invention are isolated. It has been identified by the various experiments shown in the following examples that the thus isolated substance has the structure of the formula (I).

The NCS derivatives (I) of the present invention can be utilized as medicaments in human therapy by local administration, such as the primary site of cancer and the area of tumor removal or resection, or by intracutaneous, subcutaneous, intramuscular, intravenous, and oral administration, or by external application, such as applying or spraying to local site to be treated, suppository, intravesical instillation. The dose regimen depends on administration routes, malignancy stage and grade of tumor, types of tumor, and various conditions of patients. Further, the dosages depends on the purpose, such as the prevention of metastasis to lymphatic systems after operation, or therapeutic treatment or extent of tumor regression. For example, in the case of the intravenous administration is 1–3 mg per every half day, that is twice a day on consecutive days. For local application as ointments or for oral administration, the dosage may be further increased.

The NCS derivative (I) of the present invention maintains the high biological activity due to NCS and noticeably the toxicity possessed by NCS noticeably decreased and the activity of NCS derivative of the present invention is retained for a far longer period of time than NCS in the whole blood. The NCS derivative (I) of the present invention is soluble in 1–9% of aqueous solution of sodium bicarbonate, so that this solution can be intravenously or intraarterially administered and such an administration can exert the above described properties of NCS derivatives of the present invention, namely, it will accumulate in the lymphatic system resulting into antimetastatic effect therein.

In any route of administration, the NCS derivatives (I) accumulate preferably at the tumor tissue. In the tumorous area, the NCS derivatives (I) directly separates NCS or is partially hydrolyzed to separate NCS to exert the antitumor activity, after which NCS portion and the partially half-esterified styrene-maleic acid co-polymeric portion are safely excreted out of the body in urine.

Thus, the NCS derivatives (I) of the present invention show very desirable activity as an anticancer agent.

The following examples are given for purpose of illustration of this invention and are not intended as limitations thereof.

EXAMPLE 1

Figure 1:
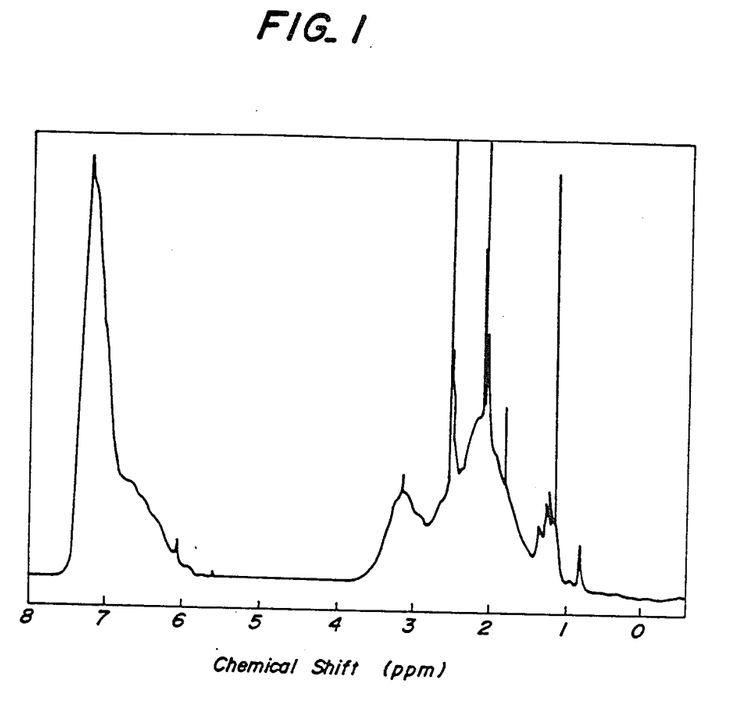
FIG. 1 is an NMR spectrum of unfractionated styrene-maleic acid anhydride copolymer to be used for the production of partially hydrolyzed styrene-maleic anhydride copolymer according to the present invention.

(1) Polymerization of styrene-maleic anhydride copolymer:

30 l of cumene was charged into a explosion proof vessel of an inner volume of 150 l, to which a homogeneous solution consisting of 3.5 kg of maleic anhydride, 20 l of cumene, 3.7 kg of styrene, and 200 g of benzoyl peroxide continuously were fed in 65 minutes while being heated at 150° C. After the feeding, stirring was carried out at 150° C. for 60 minutes. Then, the reaction mixture was cooled to room temperature. Thereafter, 30 l of n-hexane was added thereto to precipitate the polymer formed. The liquid phase was taken out and the precipitated polymer was obtained. After the polymer was pulverized, it was washed with n-hexane, followed by drying. The yield of the thus obtained polymer was 7.3 kg. The number-average molecular weight ($\overline{Mn}$) of the polymer measured by vapor pressure osmometry (abbreviated as VPO hereinafter) was 1,680. It was confirmed according to the NMR spectrum measurement that the polymer thus obtained was a copolymer of styrene and maleic anhydride in a molar ratio of 1:1. (See FIG. 1)

(2) Fractionation of styrene-maleic anhydride copolymer:

40 g of the styrene-maleic anhydride copolymer (SMA) obtained in the step (1) was dissolved in 1.4 l of acetone, and 3.8 kg of glass beads (average particle size 0.1 mm) the surface of which had been treated beforehand with a silane coupling agent were added thereto. Thereafter, the acetone was evaporated to deposit SMA on the surfaces of the glass beads.

The SMA deposited glass beads and 1.4 l of a mixed solvent of acetone and n-hexane (the volume ratio thereof being 8:92 at 25° C.) were charged into a column having an inner diameter of 80 mm and a length of 80 cm, while keeping the temperature of the system at 25° C., then three kinds of mixed solvents of acetone and n-hexane [the mixed solvents at 25° C. being (i) 0.6 l of the mixed ratio of 8:92, (ii) 3.0 l of the mixed ratio of 22:78, and (iii) 3.0 l of the mixed ratio of 38:62 in this order] were successively fed, and the liquid was eluted from the lower outlet of the column. An eluate obtained when the mixed solvent of acetone and n-hexane with the volume ratio of 38:62 was concentrated and dried under reduced pressure to obtain 9.5 g of a sample. This sample was subjected to gel permeation chromatography (abbreviated as "GPC" hereinafter) and the weight-average molecular weight ($\overline{Mw}$) was 1,510, the number average molecular weight ($\overline{Mn}$) was 1,290 ($\overline{Mw}/\overline{Mn}=1.17$).

(3) Partial hydrolysis of the fractionated SMA:

6.0 g of SMA obtained in the step (2), 5.0 g of water, 16 ml of dioxane and 0.06 g of lithium acetate were charged into a glass test tube, which was then followed by sealing, and then the contents were homogeneously dissolved at room temperature under shaking for 24 hours. Then this solution was kept at 90° C. for 17 hours and it was cooled to room temperature and the reaction mixture was taken out. The reaction mixture thus taken out was diluted two fold with dioxane and lyophilized, and then the product was dried under vacuum to obtain a light yellowish flake-like substance, which was pulverized to obtain 5.9 g of powder. The infrared absorption spectrum was measured by the KBr powder method, and it was confirmed through the optical densities at wave number of 1,780 cm$^{-1}$ and 700 cm$^{-1}$ that the powder thus obtained was partially hydrolyzed styrene-maleic anhydride copolymer (H-SMA) wherein the content of the remaining maleic anhydride ring was 47.5 mol% (the maleic anhydride ring contained in one molecule being 2.9). According to GPC, $\overline{Mw}$ was 1,560, $\overline{Mn}$ was 1,350 and $\overline{Mw}/\overline{Mn}$ was 1.16.

(4) Reaction of NCS with H-SMA:

20 g of neocarzinostatin (NCS) was dissolved in 5.0 ml of 0.8M aqueous solution of sodium bicarbonate under ice-cooling in the dark. The powdery H-SMA stepwise was added in a total amount of 0.5 g in several times and dissolved thereinto. During the reaction, the pH of the solution was kept around 8.5. The conversion of such an unreacted primary amino group originating from NCS can be determined by a method (hereinafter referred to as "TNBS" method) in which a small amount of a sample taken out from the reaction mixture 24 hours after the addition was started was diluted, and was reacted with trinitrobenzene sulfonic acid to produce a nitrobenzene derivative, which was determined based on the amount of the primary amino group spectrophotometrically by a visible absorption spectrometer at 420 nm. It was learned that the primary amino groups completely disappeared.

The thus obtained reaction mixture was transferred to a dialysis tube (Union Carbide Co., Ltd., U.S.A.) having a cut-off molecular weight of 8,000, and dialyzed for three days against aqueous 5 mM ammonium bicarbonate under ice-cooling in the dark while the exterior liquid was exchanged sometimes.

Figure 2:
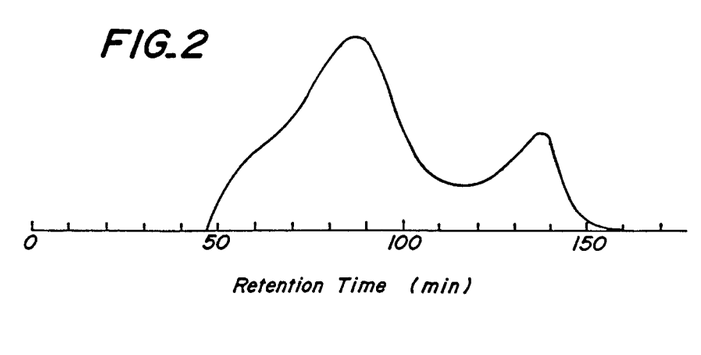
FIG. 2 is a gel-filtration profile obtained during the purification of the NCS derivative, according to the present invention.

(5) Purification of NCS derivative (I):

A half amount of the dialyzed reaction liquid was poured into a column having an inner diameter of 50 mm and a length of 60 cm (K 50/60, Pharmacia Fine Chemicals, AB, Uppsala, Sweden) packed with Sephadex G-75, and elution was carried out at a flow rate of 5.9 ml/min at 10° C. in the dark by using 5 mM aqueous ammonium bicarbonate. Absorption of the eluate was continuously monitored at the wavelength of 254 nm (FIG. 2). The eluate cut from 55 to 100 minutes after the sample injection was then lyophilized. This operation was repeated under the same conditions. The purified NCS derivatives (I) thus obtained weighed 210 mg in total. According to the elution curve of FIG. 2, mainly by-products (IV), (V), and (VI) were eluted during a retention time of 45–55 minutes. The second peak around the retention time around 140 minutes was assigned to the hydrolyzed and ring opened product of H-SMA.

Figure 3A:
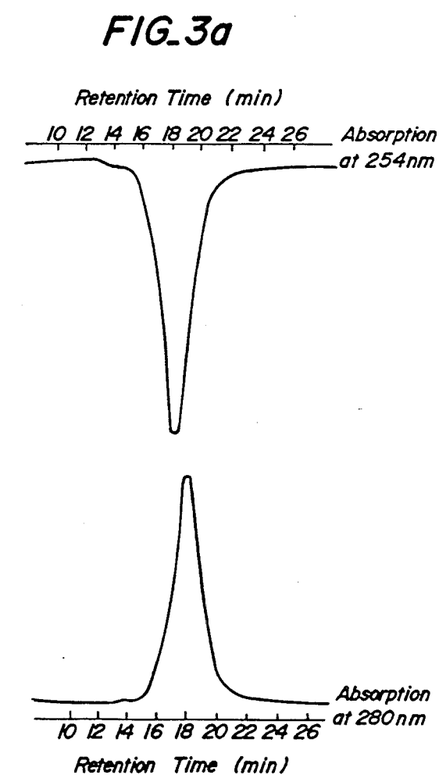
FIGS. 3a and 3b are gel permeation chromatograms (GPC) of the NCS derivative according to the present invention and NCS as a starting material thereof.
Figure 3B:
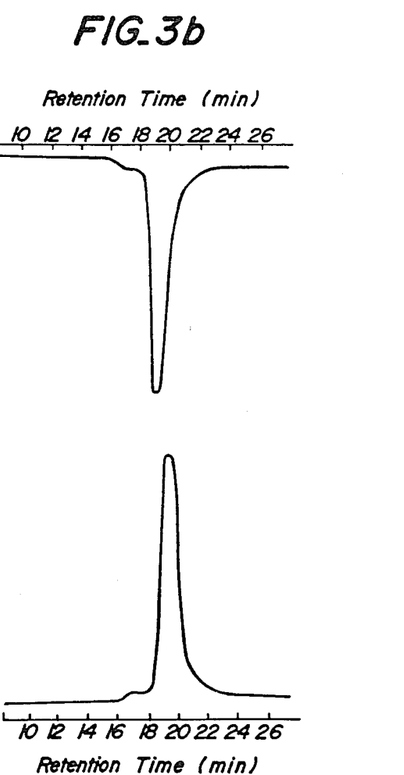

When the electrophoresis was performed by using polyacryl amide gel containing dodecyl sodium sulfate, the NCS derivative thus obtained showed a single spot. As shown in FIG. 3a, the GPC measured at pH 7.9 by using a G-3000 SW column manufactured by Toyo Soda Co., Ltd. with a mobile phase of 10 mM aqueous bicarbonate indicated a sharp peak.

The elementary analysis showed N: 10.99% by weight, C: 52.97% by weight, and H: 6.10% by weight.

The average molecular weight of the NCS derivative based on the content of the nitrogen is 13,900. The average molecular weight was calculated according to the following formula (IX):

$$\overline{M}d = \overline{M}_N \cdot N_N / N_d \quad (IX)$$

wherein $\overline{M}d$ is the average molecular weight of the NCS derivative, $M_N$ is the molecular weight of NCS (=10,700), $N_N$ is the nitrogen content according to the elementary analysis of NCS and 14.24% by weight, $N_d$ is the nitrogen content (% by weight) according to the elementary analysis of the NCS derivative. Meanwhile, the average molecular weight of NCS derivative shown in the formula (I) is $10,700 + 1,560 \times 2 = 13,820$ based on the weight average molecular weight of E-SMA of 1,560 of H-SMA obtained from the GPC. Since the above mentioned average molecular weight based on the nitrogen content is in agreement with this value, it can be understood that in NCS derivative obtained in this Example, two residues of styrene-maleic acid copolymeric residues are bonded to one NCS residue as shown by the formula (I). The average molecular weight ($\overline{M}r$) of the partially half-esterified styrene-maleic acid copolymeric residue portion contained in the NCS derivative is determined from the average molecular weight ($\overline{M}d$) of NCS derivatives thus determined according to the following formula (X):

$$\overline{M}r = (\overline{M}d - M_N)/2 \quad (X)$$

wherein $\overline{M}r$ denotes the average molecular weight of the styrene-maleic acid copolymeric residue in the NCS derivative, $\overline{M}d$ is the average molecular weight of the NCS derivative, and $M_N$ is the molecular weight of NCS (=10,700). According to this formula, $\overline{M}r$ is 1,600. This value is not largely different from the weight average molecular weight of the starting material of H-SMA being 1,560 obtained from GPC.

Although the melting point measurement was tried, no clear melting point was observed.

Figure 4A:
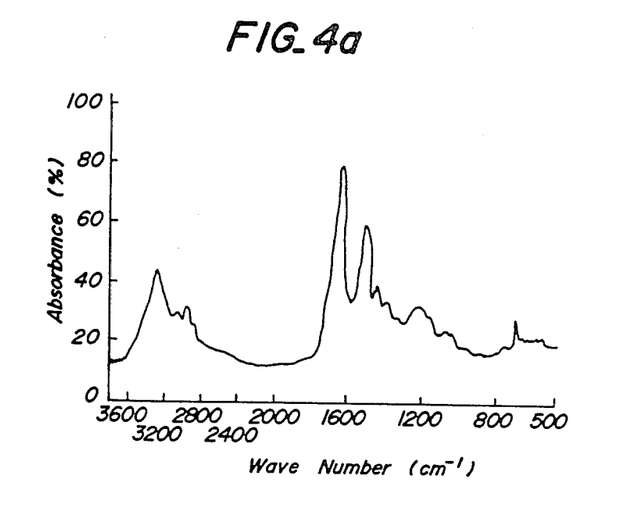
FIGS. 4a and 4b are representative IR spectra of NCS derivative according to the present invention and NCS as the starting material thereof.
Figure 4B:
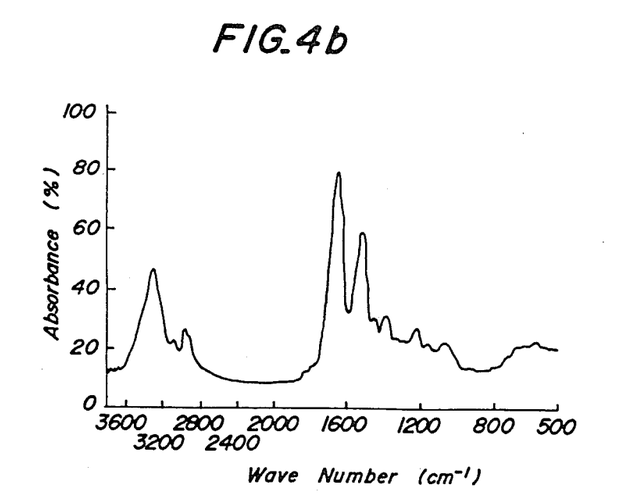
Figure 5A:
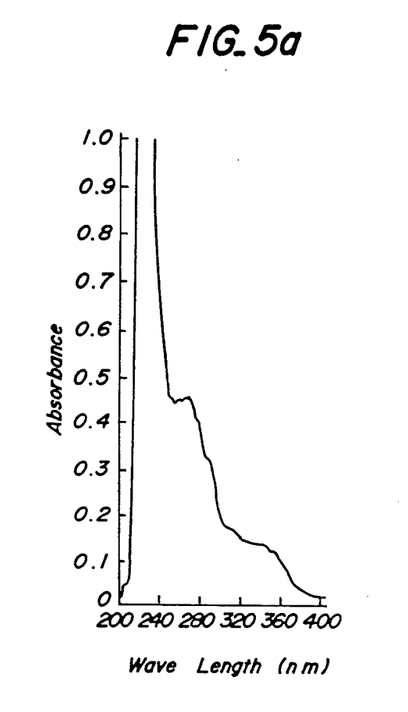
FIGS. 5a and 5b are representative UV spectra of NCS derivative according to the present invention and NCS as the starting material thereof.
Figure 5B:
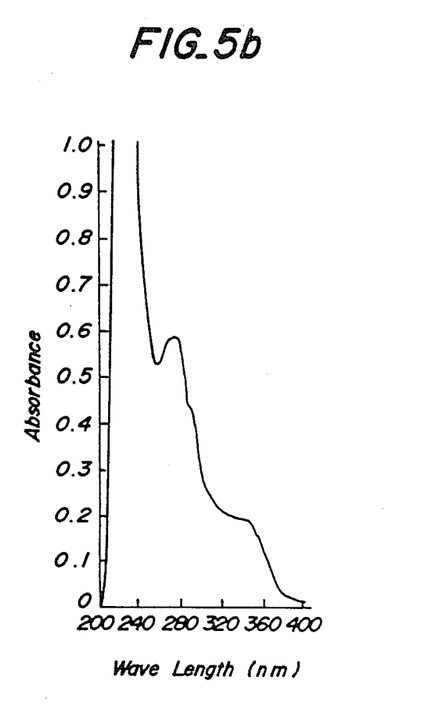

FIG. 4a shows an infrared absorption spectrum in KBr tablet method (hereinafter abbreviated as "IR spectrum") and FIG. 5a shows ultraviolet visible absorption spectrum (hereinafter abbreviated as "UV spectrum") in a 0.5 mM aqueous ammonium bicarbonate. These spectra support the structure of NCS derivative of the formula (I) according to the present invention.

EXAMPLE 2

The biological activity defined above was measured for the NCS derivative obtained in Example 1. Twenty μl aliquots of the NCS derivative having various concentrations were added to paper disc of 8 mm in diameter which had been placed on the agar plate with culture medium (Müller-Hinton) preinoculated with Sarcina lutea PCI 1001 strain. After allowing an adequate diffusion time (5 hours) at 4° C., the cultivation was resumed out at 37° C. for 12 hours. Thereby, the concentration of the diluted solution required to give an inhibition diameter of 13 mm was determined to be 1.34 when such an effective concentration in NCS was defined to be "1" and the concentrations of NCS derivatives thus determined were shown by the relative value based on the value 1 of NCS and the relative values obtained were taken as the index of the biological activity. The NCS derivative according to the present invention had the biological activity comparable to that of NCS.

Figure 6:
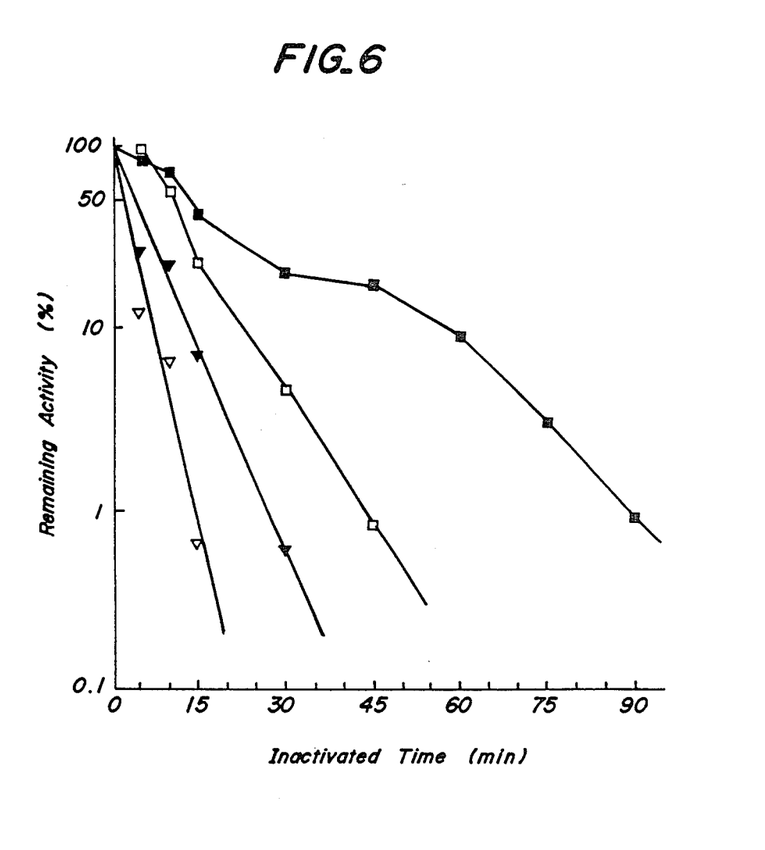
FIG. 6 is a graph showing the residual biological activity in the whole blood and in the whole serum of NCS derivative according to the present invention and NCS as the starting material thereof.

FIG. 6 shows an inactivation curve obtained by the measurement of the residual lutea biological activity of the NCS derivative while being incubated at the concentration of 100 μg/ml in the whole human blood and in the serum at 37° C. From this figure, the half-time as determined by biological activity in the whole blood and in the serum were 14 minutes and 11 minutes, respectively, with respect to NCS derivatives according to the present invention, which exhibit about 4 times that of NCS (4 minutes in the whole blood, and 2.5 minutes in the serum).

What is claimed is:

1. A substantially pure neocarzinostatin derivative having the formula (A):

(SMA)-(NCS)-(SMA)     (A)

wherein (NCS) is a divalent neocarzinostatin residue and (SMA) comprises the monovalent residue of a styrene-maleic acid copolymer having a weight-average molecular weight of from 800 to 2,500, said (NCS) residue being bonded to said (SMA) residues via amide linkages formed between primary amino groups of the neocarzinostatin molecule and carbonyl groups of the styrene-maleic acid copolymer.

2. The neocarzinostatin derivative as defined by claim 1, said styrene-maleic acid copolymer comprising (a) styrene residues, (b) maleic acid residues and (c) residues of the formula:

3. The neocarzinostatin derivative as defined by claim 2, wherein the molar ratio of the residues (a) to the sum of the residues (b) and (c) ranges from about 1:1 to 1.3:1.

4. The neocarzinostatin derivative as defined by claim 3, wherein the molar ratio of the residues (a) to the sum of the residues (b) and (c) is about 1:1.

5. The neocarzinostatin derivative as defined by claim 2, said primary amino groups of the neocarzinostatin molecule comprising the alanine residue at the N-terminal and the lysine residue at the 20th position thereof.

6. The neocarzinostatin derivative as defined by claim 1, said styrene-maleic acid copolymer comprising a partially hydrolyzed styrene-maleic anhydride copolymer.

7. The neocarzinostatin derivative as defined by claim 3, wherein the molar ratio of the residues (b) to the residues (c) ranges from 85:15 to 35:65.

8. The neocarzinostatin derivative as defined by claim 7, wherein the molar ratio of the residues (b) to the residues (c) ranges from 80:20 to 40:60.

9. A process for the preparation of a neocarzinostatin derivative, comprising reacting neocarzinostatin, in an aqueous reaction medium, with a molar excess of a partially hydrolyzed styrene-maleic anhydride copolymer, said copolymer satisfying the formulae (B) and (C):

$$800 \leq \overline{M}w \leq 2,500 \quad (B)$$

$$\overline{M}w/\overline{M}n \leq 1.5 - 1.1 - 10^{-4} \overline{M}w \quad (C)$$

wherein $\overline{M}w$ is the weight-average and $\overline{M}n$ the number-average molecular weight thereof.

10. The process as defined by claim 9, further comprising isolating the neocarzinostatin derivative of claim 10 from the reaction product thereof.

11. The process as defined by claim 10, said isolating being by gel filtration.

12. The process as defined by claim 10, comprising reacting 1.5 to 15 parts by weight of said copolymer with 1 part by weight of the neocarzinostatin.

13. The process as defined by claim 12, wherein the concentration of the total amount of the neocarzinostatin and the copolymer in said reaction medium ranges from 10 to 35% by weight.

14. The process as defined by claim 13, wherein the pH of the reaction medium ranges from 7.5 to 9.5.

15. The process as defined by claim 14, wherein the reaction is carried out at a temperature of less than 15° C. under dark conditions.

16. The process as defined by claim 11, wherein prior to said gel filtration, the reaction product is preliminarily purified.

17. The process as defined by claim 11, wherein said gel filtration is carried out utilizing a substrate having an exclusion limit of 50,000 to 150,000, with globular proteins as the molecular weight standard.

18. The process as defined by claim 9, wherein said reactant copolymer is in powder form.

19. A composition of matter comprising the neocarzinostatin derivative as defined by claim 1, and a pharmaceutically acceptable carrier therefor.

* * * * *

UNITED STATES PATENT AND TRADEMARK OFFICE
CERTIFICATE OF CORRECTION

PATENT NO. : 4,762,885

DATED : August 9, 1988

INVENTOR(S) : Maeda et al

It is certified that error appears in the above-identified patent and that said Letters Patent is hereby corrected as shown below:

Claim 9, column 14, line 6, change "$\bar{M}w/\bar{M}n \leq 1.5 - 1.1 - 10^{-4}\bar{M}w$" to --$\bar{M}w/\bar{M}n \leq 1.5 - 1.1 \times 10^{-4}\bar{M}w$--.

Signed and Sealed this

Tenth Day of April, 1990

Attest:

HARRY F. MANBECK, JR.

*Attesting Officer*    *Commissioner of Patents and Trademarks*